United States Patent
Li et al.

(10) Patent No.: US 8,263,748 B2
(45) Date of Patent: Sep. 11, 2012

(54) LYOPHILIZED FORMULATIONS OF ENGINEERED ANTI-IL-23P19 ANTIBODIES

(75) Inventors: Xuhong Li, North Potomac, MD (US); Ramesh S. Kashi, Warren, NJ (US); Aniket Badkar, Morris Plains, NJ (US)

(73) Assignee: Schering Corporation, Rahway, NJ (US)

( * ) Notice: Subject to any disclaimer, the term of this patent is extended or adjusted under 35 U.S.C. 154(b) by 0 days.

(21) Appl. No.: 13/061,076

(22) PCT Filed: Aug. 25, 2009

(86) PCT No.: PCT/US2009/054842
§ 371 (c)(1), (2), (4) Date: May 13, 2011

(87) PCT Pub. No.: WO2010/027766
PCT Pub. Date: Mar. 11, 2010

(65) Prior Publication Data
US 2011/0229490 A1    Sep. 22, 2011

Related U.S. Application Data

(60) Provisional application No. 61/092,326, filed on Aug. 27, 2008.

(51) Int. Cl.
*C07K 16/00* (2006.01)
*A61K 39/395* (2006.01)
(52) U.S. Cl. .................. 530/388.23; 424/145.1
(58) Field of Classification Search .......... None
See application file for complete search history.

(56) References Cited

U.S. PATENT DOCUMENTS

| | | | |
|---|---|---|---|
| 5,859,205 A * | 1/1999 | Adair et al. | 530/387.3 |
| 6,171,586 B1 | 1/2001 | Lam et al. | |
| 6,267,958 B1 | 7/2001 | Andya et al. | |
| 6,685,940 B2 | 2/2004 | Andya et al. | |
| 6,821,515 B1 | 11/2004 | Cleland et al. | |
| 6,991,790 B1 | 1/2006 | Lam et al. | |
| 7,060,268 B2 | 6/2006 | Andya et al. | |
| 7,247,707 B2 | 7/2007 | Besman et al. | |
| 7,514,080 B2 * | 4/2009 | Amphlett et al. | 424/133.1 |
| 7,592,004 B2 * | 9/2009 | Kaisheva et al. | 424/130.1 |
| 7,993,645 B2 * | 8/2011 | Benson et al. | 424/145.1 |
| 2006/0286103 A1 | 12/2006 | Kolhe et al. | |
| 2007/0009526 A1 | 1/2007 | Benson et al. | |
| 2007/0048315 A1 | 3/2007 | Presta | |
| 2007/0218064 A1 | 9/2007 | Benson et al. | |

FOREIGN PATENT DOCUMENTS

| | | |
|---|---|---|
| WO | WO 2004/071439 | 8/2004 |
| WO | WO 2007/024846 | 3/2007 |
| WO | WO 2007/076524 | 7/2007 |
| WO | WO 2007/147019 | 12/2007 |
| WO | WO 2008/088823 | 7/2008 |
| WO | WO 2008/103432 | 8/2008 |
| WO | WO 2008/103473 | 8/2008 |
| WO | WO 2009/043933 | 4/2009 |

OTHER PUBLICATIONS

Eduardo Padlan, Mol Immunol. Feb. 1994;31(3): 169-217.*
Portolano et al., J Immunol. Feb. 1, 1993;150(3):880-7.*
Avastin Prescribing Information—Package Insert, Jul. 2009.
Cimzia Prescribing Information—Package Insert, Nov. 2009.
Ilaris Prescribing Information—Package Insert, Jun. 2009.

* cited by examiner

*Primary Examiner* — Shulamith H Shafer
(74) *Attorney, Agent, or Firm* — Gregory R. Bellomy

(57) ABSTRACT

The present invention provides lyophilized formulations of antibodies, such as antibodies that specifically bind to human interleukin-23 p19 (IL-23p19), or antigen binding fragments thereof.

14 Claims, 7 Drawing Sheets

Batch Number: 1 (pH 5.5)
Storage Condition: 5C

Stability Test Interval (Months)

| Test | Initial (Upright) | 1M (Upright) | 3M (Upright) | 6M (Upright) | 9M (Upright) | 9M (Inverted) | 12M (Upright) | 18M (Upright) |
|---|---|---|---|---|---|---|---|---|
| Description: Lyo Powder | White firm cake | White firm cake | White firm cake | White to off white cake | White cake | White cake | White Cake | White cake |
| Reconstitution Time | 10 mins | 14 mins | 14 mins | 14 mins | 16 mins | 16 mins | 15 mins | 15 minutes |
| Description: Reconstituted Solution | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains Particulates |
| pH | 5.6 | 5.6 | 5.6 | 5.6 | 5.6 | 5.6 | 5.6 | 5.6 |
| Assay – UV Concentration (mg/mL) | 104.82 | 100.08 | 96.65 | 104.49 | 95 | 100.7 | 90.1 | 104.2 |
| SDS-PAGE reduced (% impurity) | 1.01 | 0.61 | 0.42 | 0.62 | 0.63 | 0.56 | 0.73 | 1.81 |
| HPSEC Purity (%) | | | | | | | | |
| High Molecular Wt. Species: | 1.35 | 1.68 | 1.65 | 1.79 | 1.61 | 1.67 | 1.76 | 1.20 |
| Late Eluting Peaks: | No Visible Peak | 0.04 | 0.04 | No Visible Peak | No Visible Peak | 0.02 | No Visible Peak | No visible peak |
| Monomer: | 98.6 | 98.28 | 98.3 | 98.2 | 98.4 | 98.3 | 98.2 | 98.8 |
| HP-IEX Purity (%) | | | | | | | | |
| Acidic variants: | 7.3 | 11.53 | 6.8 | 4 | 6.7 | 6.7 | 6.5 | 5.3 |
| Acidic 1: | 8.8 | 3.78 | 9 | 7.4 | 9 | 9 | 8.6 | 8.1 |
| Main: | 67.6 | 68.79 | 68.3 | 70 | 68.3 | 68.3 | 68.7 | 68.7 |
| Basic 1: | 9 | 8.89 | 8.9 | 10.4 | 9 | 9 | 9.0 | 9.9 |
| Basic 2: | 6.7 | 6.41 | 6.4 | 8.9 | 6.5 | 6.5 | 6.6 | 4.1 |
| Basic variants: | 0.7 | 0.61 | 0.6 | N/A | 0.5 | 0.5 | 0.6 | 3.8 |
| Binding ELISA | | | | | | | | |
| $EC_{50}$ (pM) | 29 | 38 | 49 | 92 | 65 | 47 | 83 | 99 |
| Potency relative to control (%) | 140 | 67 | 162 | 104 | 76 | 104 | 79 | 97 |
| Moisture (%) | 0.40 | 0.22 | 0.46 | 0.45 | 0.52 | 0.52 | 0.43 | 0.54 |

FIG. 2

Batch Number - 1 (pH 5.5) / Storage Condition - 25H

Stability Test Interval (Months)

| Test | Initial (Upright) | 1M (Upright) | 3M (Upright) | 3M (Inverted) | 6M (Upright) | 6M (Inverted) | 9M (Upright) | 9M (Inverted) | 12M (Upright) | 12M (Inverted) | 18M (Upright) |
|---|---|---|---|---|---|---|---|---|---|---|---|
| Description: Lyo Powder | White firm cake | White firm cake | White firm cake | White firm cake | White to off white cake | White to off white cake | White cake | White cake | White cake | White cake | White cake |
| Reconstituti on Time | 10 mins | 14 mins | 14 mins | 14 mins | 14 mins | 14 mins | 16 mins | 16 mins | 15 mins | 15 mins | 15 mins |
| Description: Reconstituted Solution | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates |
| pH | 5.6 | 5.6 | 5.6 | 5.6 | 5.6 | 5.6 | 5.6 | 5.6 | 5.6 | 5.6 | 5.6 |
| Assay - UV Concentration (mg/mL) | 104.82 | 102.86 | 100.4 | 98.12 | 97.55 | 103.06 | 100.4 | 106.9 | 102.5 | 108.7 | 103.3 |
| SDS-PAGE reduced | 1.01 | 0.92 | 0.59 | 0.62 | 0.44 | 0.59 | 0.29 | 0.83 | 0.55 | 0.66 | 3.75 |
| HPSEC Purity | | | | | | | | | | | |
| High Molecular Weight Peaks | 1.35 | 2.1 | 2.59 | 2.55 | 3.07 | 3.09 | 3.04 | 3.15 | 3.76 | 3.68 | 2.91 |
| Late Eluting Peaks: | No visible Peak | No visible Peak | 0.06 | 0.06 | No visible Peak | No visible Peak | No visible Peak | No visible Peak | No visible Peak | No visible Peak | No visible peak |
| Monomer | 98.6 | 97.9 | 97.3 | 97.4 | 96.9 | 96.9 | 97 | 96.9 | 96.2 | 96.3 | 97.1 |
| HP-IEX Purity | | | | | | | | | | | |
| Acidic variants: | 7.3 | 11.74 | 7 | 7 | 4.2 | 4.8 | 7.5 | 7.4 | 7.3 | 7.2 | 6.5 |
| Acidic 1: | 8.8 | 3.81 | 9.4 | 9.4 | 7.9 | 7.3 | 9.5 | 9.4 | 9.2 | 9.3 | 9.6 |
| Main: | 67.6 | 67.92 | 66.9 | 66.9 | 67.2 | 67.5 | 64.3 | 64.6 | 66.0 | 66.0 | 64.9 |
| Basic 1: | 9 | 9.35 | 9.5 | 9.5 | 11.6 | 11.4 | 10.2 | 10.2 | 10.2 | 10.3 | 11.3 |
| Basic 2: | 6.7 | 6.56 | 6.6 | 6.6 | 9.1 | 9.1 | 7 | 6.9 | 6.7 | 6.7 | 4.5 |
| Basic variants: | 0.7 | 0.62 | 0.6 | 0.6 | N/A | N/A | 1.6 | 1.4 | 0.6 | 0.5 | 3.2 |
| Other | N/A | N/A | N/A | N/A | N/A | N/A | N/A | N/A | N/A | N/A | 6.5 |
| Binding ELISA | | | | | | | | | | | |
| EC$_{50}$(pM) | 29 | 48 | 100 | 87 | 87 | 91 | 55 | 53 | 84 | 82 | 88 |
| Potency relative to control (%) | 140 | 53 | 79 | 90 | 111 | 106 | 89 | 93 | 78 | 80 | 110 |
| Moisture (%) | 0.40 | 0.44 | 0.68 | 0.63 | 0.73 | 1.03 | 1.06 | 0.93 | 1.02 | 1.10 | 1.67 |

FIG. 3

Batch Number - 1 (pH 5.5) / Storage Condition - RH4

Stability Test Interval (Months)

| Test | Initial (Upright) | 2 weeks (Upright) | 1M (Upright) | 2M (Upright) | 3M (Upright) | 3M (Inverted) | 6M (Upright) | 6M (Inverted) | 9M (Upright) |
|---|---|---|---|---|---|---|---|---|---|
| Description: Lyo Powder | White firm cake | White firm cake | White firm cake | White to off-white powder | White firm cake | White firm cake | White to off-white cake | White firm cake | White cake |
| Reconstitution Time | 10 mins. | 12 mins. | 14 mins | 14 mins | 14 mins | 14 mins | 14 mins | 14 mins | 16 mins |
| Description: Reconstituted Solution | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates |
| pH | 5.6 | 5.6 | 5.6 | 5.6 | 5.6 | 5.6 | 5.6 | 5.6 | 5.6 |
| Assay - UV Concentration (mg/mL) | 104.82 | 93.88 | 102.37 | 95.35 | 103.02 | 102.86 | 97.96 | 100.82 | 102.4 |
| SDS-PAGE reduced (% Impurity) | 1.01 | 0.32 | 1 | 0.75 | 0.42 | 0.42 | 1.63 | 1.13 | 3.56 |
| HPSEC Purity (%) | | | | | | | | | |
| High Molecular Wt. Species | 1.35 | 2.47 | 3.49 | 4.63 | 5.19 | 5.11 | 7.25 | 7.32 | 7.88 |
| Late Eluting Peaks | No Visible Peak | 0.04 | 0.05 | 0.06 | 0.07 | 0.04 | No Visible Peak | 0.02 | No Visible Peak |
| Monomer | 98.6 | 97.5 | 96.46 | 95.3 | 94.7 | 94.9 | 92.7 | 92.7 | 92.1 |
| HP-IEX Purity (%) | | | | | | | | | |
| Acidic Variants | 7.3 | 11.53 | 12.9 | 6.4 | 8.4 | 9 | 6.6 | 7.1 | 11 |
| Acidic 1 | 8.8 | 4.26 | 3.88 | 10.3 | 11.2 | 10.6 | 9.3 | 9.4 | 12.4 |
| Main | 67.6 | 66.98 | 65.14 | 61.6 | 62 | 58.2 | 58.1 | 57.5 | 57.9 |
| Basic 1 | 9 | 9.98 | 10.57 | 12.2 | 11.2 | 11.1 | 14.4 | 14.2 | 6.5 |
| Basic 2 | 6.7 | 6.57 | 6.87 | 9.4 | 6.6 | 7.3 | 11.7 | 11.8 | 6 |
| Basic variants | 0.7 | 0.68 | 0.64 | 0 | 0.5 | 3.8 | N/A | N/A | N/A |
| Other | N/A | N/A | N/A | N/A | N/A | N/A | N/A | N/A | 6.2 |
| Binding ELISA | | | | | | | | | |
| $EC_{50}$(pM) (pM) | 29 | 36 | 43 | 269 | 107 | 96 | 117 | 101 | 76 |
| Potency relative to control (%) | 140 | 63 | 60 | 83 | 74 | 82 | 82 | 92 | 65 |
| Moisture (%) | 0.40 | 0.92 | 0.71 | 0.92 | 1.01 | 1.37 | 1.52 | 1.70 | ND |

FIG. 4

Batch Number - 2 (pH 4.8)
Storage Condition - 5C

Stability Test Interval (Months)

| Test | Initial (Upright) | 1M (Upright) | 3M (Upright) | 6M (Upright) | 9M (Upright) | 12M (Upright) | 12M (Inverted) |
|---|---|---|---|---|---|---|---|
| Description: Lyo Powder | White to off-white powder | White to off-white powder | White to off-white cake | White cake | White cake | White cake | White cake |
| Reconstitution Time | 14 mins | 25 mins | 25 mins | 25 mins | 25 mins | 25 mins | 25 mins |
| Description: Reconstituted Solution | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates |
| pH | 4.9 | 4.8 | 4.9 | 4.9 | 5.0 | 4.9 | 4.9 |
| Assay – UV Concentration (mg/mL) | 108.08 | 103.84 | 111.18 | 104.3 | 104.7 | 108.1 | 103.7 |
| SDS-PAGE reduced (%impurity) | 0.64 | 1.09 | 0.89 | 0.66 | 1.07 | 1.11 | 1.19 |
| HPSEC Purity | | | | | | | |
| High Molecular Wt. Species: | 0.93 | 0.63 | 1.04 | 1.2 | 1.2 | 1.41 | 1.4 |
| Late Eluting Peaks: | 0.03 | No Visible Peak | No Visible Peak | No Visible Peak | No Visible Peak | 0.02 | 0.02 |
| Monomer: | 99 | 99.4 | 99 | 98.8 | 98.8 | 98.6 | 98.6 |
| HP-IEX Purity | | | | | | | |
| Acidic variants: | 7.4 | 7.5 | 7.4 | 14.1 | 8.5 | N/A | N/A |
| Acidic 1: | 9.9 | 9.6 | 9.8 | 5 | 9.29 | 10.21 | 10.33 |
| Main : | 68.6 | 68.7 | 68.4 | 67.1 | 68.12 | 68.19 | 68.21 |
| Basic 1: | 9.3 | 9.2 | 9.4 | 8.9 | 9.23 | 9.28 | 9.3 |
| Basic 2: | 4.9 | 4.9 | 5 | 4.5 | 4.49 | 2.67 | 2.87 |
| Basic variants : | N/A | 0.1 | N/A | N/A | 0.37 | N/A | N/A |
| Binding ELISA | | | | | | | |
| $EC_{50}$(pM) | 87 | 78 | 75 | 122 | 108 | 76 | 78 |
| Potency relative to control (%) | 104 | 128 | 108 | 75 | 61 | 126 | 123 |
| Moisture (%) | 0.33 | 0.10 | 0.25 | 0.25 | 0.3 | 0.73 | 0.48 |

FIG. 5

Batch Number - 2 (pH 4.8)
Storage Condition - 25H

| Test | Initial (Upright) | 1M (Upright) | 3M (Upright) | 6M (Upright) | 6M (Inverted) | 9M (Upright) | 12M (Upright) | 12M (Inverted) |
|---|---|---|---|---|---|---|---|---|
| Description: Lyo Powder | White to off-white powder | White to off-white powder | White to off-white cake | White cake | White cake | White cake | White cake | White cake |
| Reconstitution Time: | 14 mins. | 25 mins | 25 mins | 25 mins | 25 mins | 25 mins | 25 mins | 25 mins |
| Description: Reconstituted Solution | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates | Opalescent solution contains particulates |
| pH | 4.9 | 4.8 | 4.9 | 4.9 | 4.9 | 4.9 | 4.9 | 4.9 |
| Assay – UV Concentration (mg/mL) | 108.08 | 109.55 | 110.69 | 103 | 112.5 | 98.8 | 106.4 | 104.3 |
| SDS-PAGE reduced (% impurity) | 0.64 | 1.43 | 0.91 | 1.52 | 1.52 | 1.07 | 1.61 | 1.48 |
| HPSEC Purity | | | | | | | | |
| High Mol Wt. Species | 0.93 | 0.91 | 1.93 | 2.64 | 2.68 | 2.96 | 3.71 | 3.68 |
| Late Eluting Peaks: | 0.03 | No Visible Peak | No Visible Peak | 0.04 | 0.03 | No Visible Peak | 0.02 | 0.02 |
| Monomer: | 99 | 99.1 | 98.1 | 97.3 | 97.3 | 97 | 96.3 | 96.3 |
| HP-IEX Purity | | | | | | | | |
| Acidic variants: | 7.4 | 8.1 | 9.2 | 17.1 | 16.9 | 11.21 | N/A | N/A |
| Acidic 1: | 9.9 | 9.7 | 10 | 4.7 | 4.6 | 9.95 | 11.72 | 11.81 |
| Main : | 68.6 | 67.5 | 65.1 | 63.5 | 63.7 | 62.65 | 61.77 | 62.3 |
| Basic 1: | 9.3 | 9.6 | 10.3 | 9.8 | 9.9 | 10.75 | 10.61 | 10.73 |
| Basic 2: | 4.9 | 5.1 | 5.3 | 4.7 | 4.7 | 5.06 | 3.42 | 3.29 |
| Basic variants : | N/A | N/A | N/A | 0.2 | 0.2 | 0.39 | N/A | N/A |
| Other | N/A | N/A | N/A | N/A | N/A | N/A | N/A | N/A |
| Binding ELISA | | | | | | | | |
| $EC_{50}$ (pM) | 87 | 77 | 74 | 90 | 112 | 108 | 69 | 83 |
| Potency relative to control (%) | 104 | 131 | 109 | 100 | 81 | 61 | 127 | 115 |
| Moisture (%) | 0.33 | 0.17 | 0.82 | 0.53 | 1.06 | 0.78 | 0.86 | 0.94 |

FIG. 6

Batch Number - 2 (pH 4.8)
Storage Condition - RH4

| Test | Initial (upright) | 2Weeks (Upright) | Stability Testing Interval (Months) 1M (Upright) | 3M (Upright) | 3M (Inverted) |
|---|---|---|---|---|---|
| Description: Lyo Powder | White to off-white powder | White to off-white powder | White to off-white powder | White to off-white cake | White to off-white cake |
| Reconstitution Time | 14 mins. | 25 mins. | 25 mins | 25 mins | 25 mins |
| Description: Reconstituted Solution | Opalescent solution contains particulates | Opalescent solution contains particulates | Opalescent solution contains particulates | Opalescent solution contains particulates | Opalescent solution contains particulates |
| pH | 4.9 | 4.9 | 4.8 | 4.9 | 4.9 |
| Assay - UV Concentration (mg/mL) | 108.08 | 108.41 | 99.2 | 104.16 | 112.65 |
| SDS-PAGE reduced (% Impurity) | 0.64 | 1.03 | 1.14 | 1.96 | 1.59 |
| HPSEC Purity (%) | | | | | |
| High Molecular Wt. Species: | 0.93 | 0.79 | 1.83 | 4.92 | 4.88 |
| Late Eluting Peaks: | 0.03 | 0.02 | No Visible Peak | No Visible Peak | No Visible Peak |
| Monomer : | 99 | 99.2 | 98.2 | 95.1 | 95.1 |
| HP-IEX Purity | | | | | |
| Acidic variants: | 7.4 | 9.5 | 11.8 | 15 | 16.5 |
| Acidic 1: | 9.9 | 10.4 | 10.4 | 11.8 | 11.5 |
| Main : | 68.6 | 64.4 | 61.6 | 55 | 54.2 |
| Basic 1: | 9.3 | 10.2 | 10.6 | 12 | 11.8 |
| Basic 2: | 4.9 | 5.5 | 5.5 | 6.2 | 6.0 |
| Basic variants : | N/A | N/A | N/A | N/A | N/A |
| Other | N/A | N/A | N/A | N/A | N/A |
| Binding ELISA (pM) | | | | | |
| EC50 (pM) | 87 | 96 | 65 | 106 | 73 |
| Potency Relative to control (%) | 104 | 100 | 156 | 77 | 111 |
| Moisture (%) | 0.33 | 0.14 | 0.17 | 0.65 | 0.74 |

FIG. 7

SEQUENCE LISTING

<160> NUMBER OF SEQ ID NOS: 52

<210> SEQ ID NO 1
<211> LENGTH: 117
<212> TYPE: PRT
<213> ORGANISM: Mus musculus

<400> SEQUENCE: 1

Glu Val Gln Leu Gln Gln Ser Gly Pro Glu Leu Val Lys Thr Gly Ala
1               5                   10                  15

Ser Val Asn Ile Ser Cys Lys Ala Ser Gly Tyr Ser Phe Thr Ala Tyr
            20                  25                  30

Tyr Ile Gln Trp Val Lys Gln Ser Arg Gly Lys Ser Leu Glu Trp Ile
        35                  40                  45

Gly Tyr Ile Ser Cys Tyr Asn Gly Ala Thr Arg Tyr Asn Gln Lys Phe
    50                  55                  60

Lys Gly Lys Ala Thr Phe Thr Val Asp Thr Ser Ser Arg Thr Ala Tyr
65                  70                  75                  80

Met Gln Phe Ser Ser Leu Thr Ser Glu Asp Ser Ala Val Tyr Phe Cys
                85                  90                  95

Ala Arg Gln Gly Phe Tyr Ala Met Asp Tyr Trp Gly Gln Gly Thr Ser
            100                 105                 110

Val Thr Val Ser Ser
        115

<210> SEQ ID NO 2
<211> LENGTH: 116
<212> TYPE: PRT
<213> ORGANISM: Mus musculus

<400> SEQUENCE: 2

His Val Gln Leu Gln Gln Ser Gly Pro Glu Val Val Arg Pro Gly Ala
1               5                   10                  15

Ser Val Lys Leu Ser Cys Lys Ala Ser Gly Tyr Ile Phe Ser Ala Tyr
            20                  25                  30

Trp Met Thr Trp Val Lys Gln Arg Pro Gly Gln Gly Leu Glu Trp Ile
        35                  40                  45

Gly Gln Ile Phe Pro Val Arg Gly Ser Ala Asp Tyr Asn Glu Ile Phe
    50                  55                  60

Glu Gly Lys Ala Thr Leu Thr Val Asp Thr Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Gly Gly Gly Phe Ala Tyr Trp Gly Gln Gly Thr Leu Val
            100                 105                 110

Thr Val Ser Ala
        115

<210> SEQ ID NO 3
<211> LENGTH: 124
<212> TYPE: PRT
<213> ORGANISM: Mus musculus

<400> SEQUENCE: 3

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Lys Gln Arg Thr Gly Gln Asp Leu Glu Trp Ile
            35                  40                  45

Gly Glu Ile Tyr Pro Arg Ser Val Asn Ser Tyr Asn Glu Arg Phe
        50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Gly Asn Tyr Tyr Gly Arg Asn Tyr Gly Tyr Phe Asp
                100                 105                 110

Tyr Trp Gly Gln Gly Thr Thr Leu Thr Val Ser Ser
        115                 120

<210> SEQ ID NO 4
<211> LENGTH: 116
<212> TYPE: PRT
<213> ORGANISM: Mus musculus

<400> SEQUENCE: 4

Gln Val Gln Leu Gln Gln Ser Gly Leu Glu Leu Val Lys Pro Gly Ser
1               5                   10                  15

Ser Leu Lys Ile Ser Cys Lys Ala Ser Gly Tyr Ser Phe Thr Ser Phe
                20                  25                  30

Phe Ile His Trp Leu Lys Gln Arg Pro Gly Gln Gly Leu Glu Trp Ile
            35                  40                  45

Gly Trp Ile Phe Pro Gly Asn His Asp Val Glu Tyr Asn Glu Lys Phe
        50                  55                  60

Lys Gly Lys Ala Thr Leu Thr Ala Asp Thr Ser Ser Thr Ala Asp
65                  70                  75                  80

Met His Leu Ser Ser Leu Thr Ser Glu Asp Ser Ala Val Tyr Phe Cys
                85                  90                  95

Ala Arg Gly Gly Gly Asn Leu Pro Tyr Trp Gly Gln Gly Thr Leu Val
                100                 105                 110

Thr Val Ser Ala
        115

<210> SEQ ID NO 5
<211> LENGTH: 116
<212> TYPE: PRT
<213> ORGANISM: Mus musculus

<400> SEQUENCE: 5

His Val Gln Leu Gln Gln Ser Gly Pro Glu Leu Val Arg Pro Gly Ala
1               5                   10                  15

Ser Val Glu Leu Ser Cys Lys Ala Ser Gly Tyr Ile Phe Ile Thr Tyr
                20                  25                  30

Trp Met Thr Trp Met Lys Gln Arg Pro Gly Gln Gly Leu Glu Trp Ile

```
                35                  40                  45
Gly Gln Ile Phe Pro Ala Ser Gly Ser Ala Asp Tyr Asn Glu Met Phe
    50                  55                  60

Glu Gly Lys Ala Thr Leu Thr Val Asp Thr Ser Ser Asn Thr Ala Tyr
 65                  70                  75                  80

Met Gln Leu Ser Ser Leu Thr Ser Glu Asp Ser Ala Val Tyr Phe Cys
                85                  90                  95

Ala Arg Gly Gly Gly Phe Ala Tyr Trp Gly Gln Gly Thr Leu Val
            100                 105                 110

Thr Val Ser Ala
        115

<210> SEQ ID NO 6
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 6

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ile Phe Ile Thr Tyr
                 20                  25                  30

Trp Met Thr Trp Val Arg Gln Ala Pro Gly Gln Gly Leu Glu Trp Met
             35                  40                  45

Gly Gln Ile Phe Pro Ala Ser Gly Ser Ala Asp Tyr Asn Glu Met Phe
    50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
                          260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 7
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 7

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Ile Thr Tyr
            20                  25                  30
Trp Met Thr Trp Val Arg Gln Ala Pro Gly Gln Gly Leu Glu Trp Met
        35                  40                  45
Gly Gln Ile Phe Pro Ala Ser Gly Ser Ala Asp Tyr Asn Glu Lys Phe
    50                  55                  60
Glu Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
            85                  90                  95
Ala Arg Gly Gly Gly Gly Phe Ala Tyr Trp Gly Gln Gly Thr Leu Val
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
            130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
```

```
                        165                 170                 175
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 8
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Ala Gln Lys Leu
    50                  55                  60

Gln Gly Arg Val Thr Met Thr Thr Asp Thr Ser Thr Ser Thr Ala Tyr
```

```
              65                  70                  75                  80
Met Glu Leu Arg Ser Leu Arg Ser Asp Asp Thr Ala Val Tyr Tyr Cys
                            85                  90                  95

Ala Arg Gly Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 9
<211> LENGTH: 113
<212> TYPE: PRT
<213> ORGANISM: Mus musculus

<400> SEQUENCE: 9

Asn Val Val Met Thr Gln Thr Pro Leu Thr Leu Ser Val Thr Ile Gly
```

```
                1               5                   10                  15
Gln Pro Ala Ser Ile Ser Cys Lys Ser Ser Gln Ser Leu Leu Asp Ser
                    20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
50                      55                  60

Asp Arg Phe Thr Gly Ser Gly Ser Gly Thr Asp Phe Thr Leu Lys Ile
65                  70                  75                      80

Ser Arg Val Glu Ala Glu Asp Leu Gly Leu Tyr Tyr Cys Trp Gln Gly
                85                  90                  95

Thr His Phe Pro Phe Thr Phe Gly Ser Gly Thr Lys Leu Glu Ile Lys
                    100                 105                 110

Arg

<210> SEQ ID NO 10
<211> LENGTH: 108
<212> TYPE: PRT
<213> ORGANISM: Mus musculus

<400> SEQUENCE: 10

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Glu Lys Trp Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Ser
65                  70                  75                      80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg
            100                 105

<210> SEQ ID NO 11
<211> LENGTH: 111
<212> TYPE: PRT
<213> ORGANISM: Mus musculus

<400> SEQUENCE: 11

Ser Gln Ala Val Val Thr Gln Glu Ser Ala Leu Thr Thr Ser Pro Gly
1               5                   10                  15

Glu Thr Val Thr Leu Thr Cys Arg Ser Ser Thr Gly Ala Val Ile Thr
                20                  25                  30

Ser Asn Asp Ala Asn Trp Val Gln Glu Lys Pro Asp His Ser Phe Thr
            35                  40                  45

Gly Leu Ile Gly Gly Thr Asn Asn Arg Ala Pro Gly Val Pro Ala Arg
        50                  55                  60

Phe Ser Gly Ser Leu Ile Gly Asp Lys Ala Ala Leu Thr Ile Thr Gly
65                  70                  75                      80

Ala Gln Thr Glu Asp Glu Ala Ile Tyr Phe Cys Ala Leu Trp Tyr Ser
                85                  90                  95

Asn His Trp Val Phe Gly Gly Gly Thr Lys Leu Thr Val Leu Gly
            100                 105                 110
```

<210> SEQ ID NO 12
<211> LENGTH: 108
<212> TYPE: PRT
<213> ORGANISM: Mus musculus

<400> SEQUENCE: 12

```
Asp Ile Gln Met Thr Gln Ser Pro Val Ser Leu Ser Ala Ser Val Gly
1               5                   10                  15

Glu Thr Val Thr Ile Thr Cys Arg Ala Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Phe Gly Thr Pro Leu
                85                  90                  95

Thr Phe Gly Ala Gly Thr Lys Leu Asp Leu Lys Arg
            100                 105
```

<210> SEQ ID NO 13
<211> LENGTH: 108
<212> TYPE: PRT
<213> ORGANISM: Mus musculus

<400> SEQUENCE: 13

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr Gln Phe Ser Leu Lys Ile Asn Arg Leu Gln Pro
65                  70                  75                  80

Glu Asp Phe Gly Arg Tyr Phe Cys Gln His His Tyr Gly Ile Pro Phe
                85                  90                  95

Thr Phe Gly Ser Gly Thr Lys Leu Glu Ile Lys Arg
            100                 105
```

<210> SEQ ID NO 14
<211> LENGTH: 214
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(108)
<223> OTHER INFORMATION: Variable Domain

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45
```

```
Tyr Asn Ala Lys Thr Leu Ala Glu Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Gly Ile Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 10
<212> TYPE: PRT
<213> ORGANISM: Mus musculus

<400> SEQUENCE: 15

Gly Tyr Ser Phe Thr Ala Tyr Tyr Ile Gln
 1               5                  10

<210> SEQ ID NO 16
<211> LENGTH: 10
<212> TYPE: PRT
<213> ORGANISM: Mus musculus

<400> SEQUENCE: 16

Gly Tyr Ile Phe Ser Ala Tyr Trp Met Thr
 1               5                  10

<210> SEQ ID NO 17
<211> LENGTH: 10
<212> TYPE: PRT
<213> ORGANISM: Mus musculus

<400> SEQUENCE: 17

Gly Tyr Thr Phe Thr Ser Tyr Gly Ile Ser
 1               5                  10

<210> SEQ ID NO 18
<211> LENGTH: 10
<212> TYPE: PRT
<213> ORGANISM: Mus musculus

<400> SEQUENCE: 18

Gly Tyr Ser Phe Thr Ser Phe Phe Ile His
 1               5                  10

<210> SEQ ID NO 19
```

```
<211> LENGTH: 10
<212> TYPE: PRT
<213> ORGANISM: Mus musculus

<400> SEQUENCE: 19

Gly Tyr Ile Phe Ile Thr Tyr Trp Met Thr
1               5                   10

<210> SEQ ID NO 20
<211> LENGTH: 17
<212> TYPE: PRT
<213> ORGANISM: Mus musculus

<400> SEQUENCE: 20

Tyr Ile Ser Cys Tyr Asn Gly Ala Thr Arg Tyr Asn Gln Lys Phe Lys
1               5                   10                  15

Gly

<210> SEQ ID NO 21
<211> LENGTH: 17
<212> TYPE: PRT
<213> ORGANISM: Mus musculus

<400> SEQUENCE: 21

Gln Ile Phe Pro Val Arg Gly Ser Ala Asp Tyr Asn Glu Ile Phe Glu
1               5                   10                  15

Gly

<210> SEQ ID NO 22
<211> LENGTH: 17
<212> TYPE: PRT
<213> ORGANISM: Mus musculus

<400> SEQUENCE: 22

Glu Ile Tyr Pro Arg Ser Val Asn Ser Tyr Tyr Asn Glu Arg Phe Lys
1               5                   10                  15

Gly

<210> SEQ ID NO 23
<211> LENGTH: 17
<212> TYPE: PRT
<213> ORGANISM: Mus musculus

<400> SEQUENCE: 23

Trp Ile Phe Pro Gly Asn His Asp Val Glu Tyr Asn Glu Lys Phe Lys
1               5                   10                  15

Gly

<210> SEQ ID NO 24
<211> LENGTH: 17
<212> TYPE: PRT
<213> ORGANISM: Mus musculus

<400> SEQUENCE: 24

Gln Ile Phe Pro Ala Ser Gly Ser Ala Asp Tyr Asn Glu Met Phe Glu
1               5                   10                  15

Gly

<210> SEQ ID NO 25
<211> LENGTH: 17
<212> TYPE: PRT
<213> ORGANISM: Artificial Sequence
<220> FEATURE:
```

```
<223> OTHER INFORMATION: Rodent CDR with one amino acid substitution

<400> SEQUENCE: 25

Gln Ile Phe Pro Ala Ser Gly Ser Ala Asp Tyr Asn Glu Lys Phe Glu
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Rodent CDR with four amino acid substitutions

<400> SEQUENCE: 26

Gln Ile Phe Pro Ala Ser Gly Ser Ala Asp Tyr Ala Gln Lys Leu Gln
1               5                   10                  15

Gly

<210> SEQ ID NO 27
<211> LENGTH: 8
<212> TYPE: PRT
<213> ORGANISM: Mus musculus

<400> SEQUENCE: 27

Gln Gly Phe Tyr Ala Met Asp Tyr
1               5

<210> SEQ ID NO 28
<211> LENGTH: 7
<212> TYPE: PRT
<213> ORGANISM: Mus musculus

<400> SEQUENCE: 28

Gly Gly Gly Gly Phe Ala Tyr
1               5

<210> SEQ ID NO 29
<211> LENGTH: 15
<212> TYPE: PRT
<213> ORGANISM: Mus musculus

<400> SEQUENCE: 29

Gly Gly Asn Tyr Tyr Gly Arg Asn Tyr Gly Asp Tyr Phe Asp Tyr
1               5                   10                  15

<210> SEQ ID NO 30
<211> LENGTH: 7
<212> TYPE: PRT
<213> ORGANISM: Mus musculus

<400> SEQUENCE: 30

Gly Gly Gly Asn Leu Pro Tyr
1               5

<210> SEQ ID NO 31
<211> LENGTH: 7
<212> TYPE: PRT
<213> ORGANISM: Mus musculus

<400> SEQUENCE: 31

Gly Gly Gly Gly Phe Ala Tyr
1               5
```

```
<210> SEQ ID NO 32
<211> LENGTH: 16
<212> TYPE: PRT
<213> ORGANISM: Mus musculus

<400> SEQUENCE: 32

Lys Ser Ser Gln Ser Leu Leu Asp Ser Asp Gly Lys Thr Tyr Leu Asn
1               5                   10                  15

<210> SEQ ID NO 33
<211> LENGTH: 11
<212> TYPE: PRT
<213> ORGANISM: Mus musculus

<400> SEQUENCE: 33

Arg Ala Ser Glu Asn Ile Tyr Ser Tyr Leu Ala
1               5                   10

<210> SEQ ID NO 34
<211> LENGTH: 14
<212> TYPE: PRT
<213> ORGANISM: Mus musculus

<400> SEQUENCE: 34

Arg Ser Ser Thr Gly Ala Val Ile Thr Ser Asn Asp Ala Asn
1               5                   10

<210> SEQ ID NO 35
<211> LENGTH: 11
<212> TYPE: PRT
<213> ORGANISM: Mus musculus

<400> SEQUENCE: 35

Arg Thr Ser Glu Asn Ile Tyr Ser Tyr Leu Ala
1               5                   10

<210> SEQ ID NO 36
<211> LENGTH: 11
<212> TYPE: PRT
<213> ORGANISM: Mus musculus

<400> SEQUENCE: 36

Arg Thr Ser Glu Asn Ile Tyr Ser Tyr Leu Ala
1               5                   10

<210> SEQ ID NO 37
<211> LENGTH: 7
<212> TYPE: PRT
<213> ORGANISM: Mus musculus

<400> SEQUENCE: 37

Leu Val Ser Lys Leu Asp Ser
1               5

<210> SEQ ID NO 38
<211> LENGTH: 7
<212> TYPE: PRT
<213> ORGANISM: Mus musculus

<400> SEQUENCE: 38

Asn Ala Lys Thr Leu Ala Glu
1               5

<210> SEQ ID NO 39
<211> LENGTH: 7
<212> TYPE: PRT
```

<213> ORGANISM: Mus musculus

<400> SEQUENCE: 39

Gly Thr Asn Asn Arg Ala Pro
1               5

<210> SEQ ID NO 40
<211> LENGTH: 7
<212> TYPE: PRT
<213> ORGANISM: Mus musculus

<400> SEQUENCE: 40

Asn Ala Lys Thr Leu Ala Glu
1               5

<210> SEQ ID NO 41
<211> LENGTH: 7
<212> TYPE: PRT
<213> ORGANISM: Mus musculus

<400> SEQUENCE: 41

Asn Ala Lys Thr Leu Ala Glu
1               5

<210> SEQ ID NO 42
<211> LENGTH: 9
<212> TYPE: PRT
<213> ORGANISM: Mus musculus

<400> SEQUENCE: 42

Trp Gln Gly Thr His Phe Pro Phe Thr
1               5

<210> SEQ ID NO 43
<211> LENGTH: 9
<212> TYPE: PRT
<213> ORGANISM: Mus musculus

<400> SEQUENCE: 43

Gln His His Tyr Gly Thr Pro Phe Thr
1               5

<210> SEQ ID NO 44
<211> LENGTH: 9
<212> TYPE: PRT
<213> ORGANISM: Mus musculus

<400> SEQUENCE: 44

Ala Leu Trp Tyr Ser Asn His Trp Val
1               5

<210> SEQ ID NO 45
<211> LENGTH: 9
<212> TYPE: PRT
<213> ORGANISM: Mus musculus

<400> SEQUENCE: 45

Gln His His Tyr Gly Ile Pro Phe Thr
1               5

<210> SEQ ID NO 46
<211> LENGTH: 9
<212> TYPE: PRT
<213> ORGANISM: Mus musculus

<400> SEQUENCE: 46

Gln His His Tyr Gly Ile Pro Phe Thr
1               5

<210> SEQ ID NO 47
<211> LENGTH: 170
<212> TYPE: PRT
<213> ORGANISM: Homo sapiens

<400> SEQUENCE: 47

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 48
<211> LENGTH: 175
<212> TYPE: PRT
<213> ORGANISM: Mus musculus

<400> SEQUENCE: 48

Val Pro Arg Ser Ser Pro Asp Trp Ala Gln Cys Gln Gln Leu Ser
1               5                   10                  15

Arg Asn Leu Cys Met Leu Ala Trp Asn Ala His Ala Pro Ala Gly His
            20                  25                  30

Met Asn Leu Leu Arg Glu Glu Asp Glu Glu Thr Lys Asn Asn Val
        35                  40                  45

Pro Arg Ile Gln Cys Glu Asp Gly Cys Asp Pro Gln Gly Leu Lys Asp
    50                  55                  60

Asn Ser Gln Phe Cys Leu Gln Arg Ile Arg Gln Gly Leu Ala Phe Tyr
65                  70                  75                  80

Lys His Leu Leu Asp Ser Asp Ile Phe Lys Gly Glu Pro Ala Leu Leu
                85                  90                  95

Pro Asp Ser Pro Met Glu Gln Leu His Thr Ser Leu Leu Gly Leu Ser
            100                 105                 110

Gln Leu Leu Gln Pro Glu Asp His Pro Arg Glu Thr Gln Gln Met Pro
        115                 120                 125

Ser Leu Ser Ser Ser Gln Gln Trp Gln Arg Pro Leu Leu Arg Ser Lys
    130                 135                 140

```
Ile Leu Arg Ser Leu Gln Ala Phe Leu Ala Ile Ala Ala Arg Val Phe
145                 150                 155                 160

Ala His Gly Ala Ala Thr Leu Thr Glu Pro Leu Val Pro Thr Ala
                165                 170                 175
```

<210> SEQ ID NO 49
<211> LENGTH: 1398
<212> TYPE: DNA
<213> ORGANISM: Artificial Sequence
<220> FEATURE:
<223> OTHER INFORMATION: Human constant and framework regions, rodent CDRs

<400> SEQUENCE: 49

```
atggctgtgc tgggctgct  gttctgcctg gtgacattcc caagctgtgt gctgtcccag    60
gtgcagctgg tgcagtctgg cgctgaggtg aagaagcctg gcgcctccgt gaaggtctcc   120
tgcaaggctt ctggctacat cttcatcacc tactggatga cctgggtgcg gcaggcccct   180
ggccaggggc tggagtggat gggccagatc ttccctgcca gcggctctgc agactacaac   240
gagaagttcg aaggcagagt caccatgacc acagacacat ccaccagcac agcctacatg   300
gagctgagga gcctgagatc tgacgacacc gccgtgtatt actgtgccag aggcggtggc   360
ggattcgctt actggggcca gggcaccctg gtcaccgtct ccagcgctag caccaagggc   420
ccatcggtct tccccctggc accctcctcc aagagcacct ctgggggcac agcggccctg   480
ggctgcctgg tcaaggacta cttccccgaa ccggtgacgg tgtcgtggaa ctcaggcgcc   540
ctgaccagcg gcgtgcacac cttcccggct gtcctacagt cctcaggact ctactccctc   600
agcagcgtgg tgaccgtgcc ctccagcagc ttgggcaccc agacctacat ctgcaacgtg   660
aatcacaagc ccagcaacac caaggtggac aagaaagttg agcccaaatc ttgtgacaaa   720
actcacacat gcccaccgtg cccagcacct gaactcctgg ggggaccgtc agtcttcctc   780
ttccccccaa acccaaggac accctcatg atctcccgga cccctgaggt cacatgcgtg   840
gtggtggacg tgagccacga agaccctgag gtcaagttca actggtacgt ggacggcgtg   900
gaggtgcata atgccaagac aaagccgcgg gaggagcagt acaacagcac gtaccgtgtg   960
gtcagcgtcc tcaccgtcct gcaccaggac tggctgaatg gcaaggagta caagtgcaag  1020
gtctccaaca agccctccc agccccatc gagaaaacca tctccaaagc caaagggcag  1080
ccccgagaac cacaggtgta caccctgccc ccatcccggg atgagctgac caagaaccag  1140
gtcagcctga cctgcctggt caaaggcttc tatcccagcg acatcgccgt ggagtgggag  1200
agcaatgggc agccggagaa caactacaag accacgcctc ccgtgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaatga                                                1398
```

<210> SEQ ID NO 50
<211> LENGTH: 702
<212> TYPE: DNA
<213> ORGANISM: Artificial Sequence
<220> FEATURE:
<223> OTHER INFORMATION: Human constant and framework regions, rodent CDRs

<400> SEQUENCE: 50

```
atggctccag tgcagctgct ggggctgctg gtgctgttcc tgccagccat gagatgtgat    60
atccagatga cccagtctcc atcctccctg tctgcctctg tgggcgacag agtgaccatc   120
```

```
acctgcagga ccagcgagaa catctacagc tacctggcct ggtatcagca gaagccaggg    180 aaggcccta agctgctgat ctataacgcc aagaccctgg ctgaaggggt gccatccagg    240
ttcagcggca gcggctctgg gacagacttc accctgacca tcagcagcct gcagcctgag    300
gacttcgcca cctactactg tcagcaccac tacggaattc cattcacctt cggccagggc    360
accaaggtgg agatcaagcg tacggtggct gcaccatctg tgttcatctt ccctccatct    420
gatgagcagc tgaagtctgg aactgcctcc gtggtgtgcc tgctgaataa cttctatccc    480
agagaggcca aggtgcagtg gaaggtggat aacgccctcc agagcggcaa ctcccaggag    540
agcgtgacag agcaggacag caaggacagc acctacagcc tgagcagcac cctgaccctg    600
agcaaagcag actacgagaa acacaaggtg tacgcctgcg aggtgaccca tcagggcctg    660
agcagccccg tgacaaagag cttcaacagg ggagagtgtt aa                      702
```

<210> SEQ ID NO 51
<211> LENGTH: 19
<212> TYPE: PRT
<213> ORGANISM: Mus musculus

<400> SEQUENCE: 51

Met Ala Val Leu Gly Leu Leu Phe Cys Leu Val Thr Phe Pro Ser Cys
1               5                   10                  15

Val Leu Ser

<210> SEQ ID NO 52
<211> LENGTH: 19
<212> TYPE: PRT
<213> ORGANISM: Rattus norvegicus

<400> SEQUENCE: 52

Met Ala Pro Val Gln Leu Leu Gly Leu Leu Val Leu Phe Leu Pro Ala
1               5                   10                  15

Met Arg Cys

LYOPHILIZED FORMULATIONS OF ENGINEERED ANTI-IL-23P19 ANTIBODIES

FIELD OF THE INVENTION

The present invention relates generally to lyophilized formulations of therapeutic antibodies.

BACKGROUND OF THE INVENTION

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12β1, which is shared by the IL-12 receptor. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23. See, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948).

Recent studies, through the use of p40 KO mice, have shown that blockade of both IL-23 and IL-12 is an effective treatment for various inflammatory and autoimmune disorders. However, the blockade of IL-12 through p40 appears to have various systemic consequences such as increased susceptibility to opportunistic microbial infections. Bowman et al. (2006) *Curr. Opin. Infect. Dis.* 19:245. Accordingly, specific blockade of the p19 subunit of IL-23 is preferred in the treatment of human disease because it interferes with the activity of IL-23 without interfering with the activity of IL-12.

Therapeutic antibodies may be used to block cytokine activity. A significant limitation in using antibodies as a therapeutic agent in vivo is the immunogenicity of the antibodies. As most monoclonal antibodies are derived from non-human species, repeated use in humans results in the generation of an immune response against the therapeutic antibody. Such an immune response results in a loss of therapeutic efficacy at a minimum, and potentially a fatal anaphylactic response. Accordingly, antibodies of reduced immunogenicity in humans, such as humanized or fully human antibodies, are preferred for treatment of human subjects. Exemplary therapeutic antibodies to IL-23p19 are disclosed in U.S. Patent Application Publication No. 2007/0009526, and in International Patent Publication Nos. WO 2007/076524, WO 2007/024846, WO 2007/147019, and WO 2009/043933 the disclosures of which are hereby incorporated by reference in their entireties. Additional humanized anti-IL-23p19 antibodies are disclosed in commonly assigned applications published as International Patent Publication Nos. WO 2008/103432 and WO 2008/103473, and in commonly-assigned U.S. Patent Application Publication No. 2007/0048315, the disclosures of which are hereby incorporated by reference in their entireties.

Antibodies for use in human subjects must be stored prior to use and transported to the point of administration. Reproducibly attaining a desired level of antibody drug in a subject requires that the drug be stored in a formulation that maintains the bioactivity of the drug. The need exists for formulations of anti-human IL-23p19 antibodies for use, e.g., in treatment of inflammatory, autoimmune, and proliferative disorders. Preferably, such formulations will exhibit a long half-life, be stable when stored and transported, and will be amenable to administration at high concentrations, e.g. for use in subcutaneous administration, and low concentrations, e.g. for intravenous administration.

SUMMARY OF THE INVENTION

The present invention provides lyophilized formulations of binding compounds that bind to human IL-23p19, which binding compounds are defined as human or humanized anti-human IL-23p19 antibodies, or antigen-binding fragments thereof.

In one embodiment, the lyophilized formulation comprises a human or humanized anti-IL-23p19 antibody (or antigen-binding fragment thereof), sodium citrate, polysorbate 80 and sucrose. In various embodiments the pH of the formulation after reconstitution with water is 4.8 (±0.4), or 4.8 (±0.2), such as between 4.6 and 5.0, e.g. about 4.4, 4.6, 4.7, 4.8, 4.9, 5.0 or 5.2. In other embodiments, the pH is about 5.5.

In some embodiments, the lyophilized formulation enables reconstitution of the antibody (or antigen binding fragment thereof) at a concentration of about 25 mg/mL or higher, about 50 mg/mL or higher, about 75 mg/mL or higher or about 100 mg/mL or higher.

In one embodiment, polysorbate 80 derived from vegetable (non-animal) sources is present in the lyophilized formulation at a weight ratio of about 0.2% compared with the antibody (or antigen binding fragment thereof). In another embodiment, sucrose is present in the lyophilized formulation at a weight ratio of about 70% compared with the antibody (or antigen binding fragment thereof). In yet another embodiment, the sodium citrate buffer is present in the lyophilized formulation at a total weight ratio of about 2.4% compared with the antibody (or antigen binding fragment thereof).

In other embodiments, the lyophilized formulation of anti-human IL-23p19 antibody, or antigen binding fragment thereof of the present invention is made by lyophilizing a pre-lyophilization solution comprising 5-25 mg/mL anti-human IL-23p19 antibody, or antigen binding fragment thereof; about 50 mM sucrose; about 0.05 mg/mL polysorbate 80; and about 2.5 mM citrate buffer at pH 4.4-5.2. In one embodiment, the pre-lyophilization solution comprises antibody, or antigen-binding fragment thereof, at about 25 mg/mL. In one embodiment, the pre-lyophilization solution is about pH 4.8.

In yet other embodiments, the lyophilized formulation of anti-human IL-23p19 antibody, or antigen binding fragment thereof, of the present invention, when reconstituted, comprises 25-100 mg/mL anti-human IL-23p19 antibody, or antigen binding fragment thereof; about 200 mM sucrose; about 0.2 mg/mL polysorbate 80; and about 10 mM citrate buffer at pH 4.4 to 5.2. In one embodiment, the reconstituted solutions comprises antibody, or antigen-binding fragment thereof, at about 100 mg/mL. In one embodiment, the reconstituted solution is at about pH 4.8.

In still further embodiments, the lyophilized formulation is provided in a glass vial. In various embodiments, the glass vial contains about 5, 10, 15, 20, 25, 30, 40, 50, 60, 67.5, 75, 100, 150, 200, 300, 400, 500 mg/vial or more.

Exemplary binding compounds for use in the lyophilized formulations of the present invention comprise an antibody light chain variable domain, or antigen binding fragment thereof, having one, two or three CDRs selected from the group consisting of SEQ ID NOs: 32-46. In one embodiment, the binding compound of the present invention comprises a light chain variable domain comprising a CDRL1 selected from the group consisting of SEQ ID NOs: 32-36; a CDRL2 selected from the group consisting of SEQ ID NOs: 37-41; and a CDRL3 selected from the group consisting of SEQ ID NOs: 42-46.

In one embodiment, the binding compound for use in the lyophilized formulations of the present invention comprises an antibody heavy chain variable domain, or antigen binding fragment thereof, having one, two or three CDRs selected from the group consisting of SEQ ID NOs: 15-31. In one embodiment, the binding compound of the present invention comprises a heavy chain variable domain comprising a CDRH1 selected from the group consisting of SEQ ID NOs: 15-19; a CDRH2 selected from the group consisting of SEQ ID NOs: 20-26; and a CDRH3 selected from the group consisting of SEQ ID NOs: 27-31.

In some embodiments the light chain and/or heavy chain variable domains comprise a variant of one or more of the CDRs. In various embodiments the variant domain comprises up to 1, 2, 3, 4, 5 or more conservatively modified amino acid residues relative to the sequence of the respective SEQ ID NOs. Conservative amino acid substitutions are provided at Table 1.

In some embodiments the light chain variable domain comprises residues 1-108 of SEQ ID NO: 14 or a variant thereof. In some embodiments the heavy chain variable domain comprises a sequence selected from the group consisting of residues 1-116 of SEQ ID NOs: 6-8, i.e. SEQ ID NO: 6, SEQ ID NO: 7 or SEQ ID NO: 8. In various embodiments the variant variable domain comprises up to 1, 2, 3, 4, 5, 6, 7, 8, 9, 10, 15, 20, 30, 40 or 50 or more conservatively modified amino acid residues relative to the sequence of the respective SEQ ID NOs. In yet a further embodiment, the binding compound comprises a light chain variable domain and a heavy chain variable domain, or the antigen binding fragments thereof, described in this paragraph.

In one embodiment the binding compound comprises a light chain sequence of SEQ ID NO: 14 and/or a heavy chain sequence selected from the group consisting of SEQ ID NOs: 6-8.

In other embodiments the binding compound of the present invention comprises a light chain variable domain, or an antigen binding fragment thereof, consisting essentially of residues 1-108 of SEQ ID NO: 14, and/or a heavy chain variable domain, or an antigen binding fragment thereof, consisting essentially of a sequence selected from the group consisting of residues 1-116 of SEQ ID NOs: 6-8, such as SEQ ID NO: 6, SEQ ID NO: 7 or SEQ ID NO: 8.

In other embodiments the binding compound of the present invention comprises a light chain variable domain, or an antigen binding fragment thereof, having at least 75%, 90%, 95%, 98% or 99% sequence homology with residues 1-108 of SEQ ID NO: 14, and/or a heavy chain variable domain, or an antigen binding fragment thereof, having at least 75%, 90%, 95%, 98% or 99% sequence homology with a sequence selected from the group consisting of residues 1-116 of SEQ ID NOs: 6-8, such as SEQ ID NO: 6, SEQ ID NO: 7 or SEQ ID NO: 8.

In some embodiments, the binding compound of the present invention further comprises a heavy chain comprising a γ1, γ2, γ3, or γ4 human heavy chain constant region or a variant thereof. In various embodiments the binding compound comprises a light chain comprising a lambda or a kappa human light chain constant region.

In various embodiments the binding compound of the present invention is an antibody fragment selected from the group consisting of, e.g., Fab, Fab', Fab'-SH, Fv, scFv, F(ab')$_2$, and a diabody.

In other embodiments the invention relates to a lyophilized formulation of a human or humanized anti-IL-23p19 antibody, or antigen binding fragment thereof, for use in treating disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

The present invention provides a vessel (e.g., a glass vial) comprising any of the lyophilized formulations set forth herein. The present invention also provides an injection device (e.g., hypodermic needle and syringe, autoinjector, lyophilization cartridge) comprising a diluent and lyophilized formulation of a human or humanized anti-IL-23p19 antibody, or antigen binding fragment thereof.

BRIEF DESCRIPTION OF THE DRAWINGS

FIG. 2 shows stability data (18 months) for lyophilized formulations of a humanized anti-human IL-23p19 antibody at pH 5.5 stored at 5° C., as discussed in greater detail in Example 2.

FIG. 3 shows stability data (18 months) for lyophilized formulations of a humanized anti-human IL-23p19 antibody at pH 5.5 stored at 25H, as discussed in greater detail in Example 2.

FIG. 4 shows stability data (9 months) for lyophilized formulations of a humanized anti-human IL-23p19 antibody at pH 5.5 stored at RH4, as discussed in greater detail in Example 2.

FIG. 5 shows stability data (12 months) for lyophilized formulations of a humanized anti-human IL-23p19 antibody at pH 4.8 stored at 5° C., as discussed in greater detail in Example 2.

FIG. 6 shows stability data (12 months) for lyophilized formulations of a humanized anti-human IL-23p19 antibody at pH 4.8 stored at 25H, as discussed in greater detail in Example 2.

FIG. 7 shows stability data (3 months) for lyophilized formulations of a humanized anti-human IL-23p19 antibody at pH 4.8 stored at RH4, as discussed in greater detail in Example 2.

DETAILED DESCRIPTION

Figure 1:
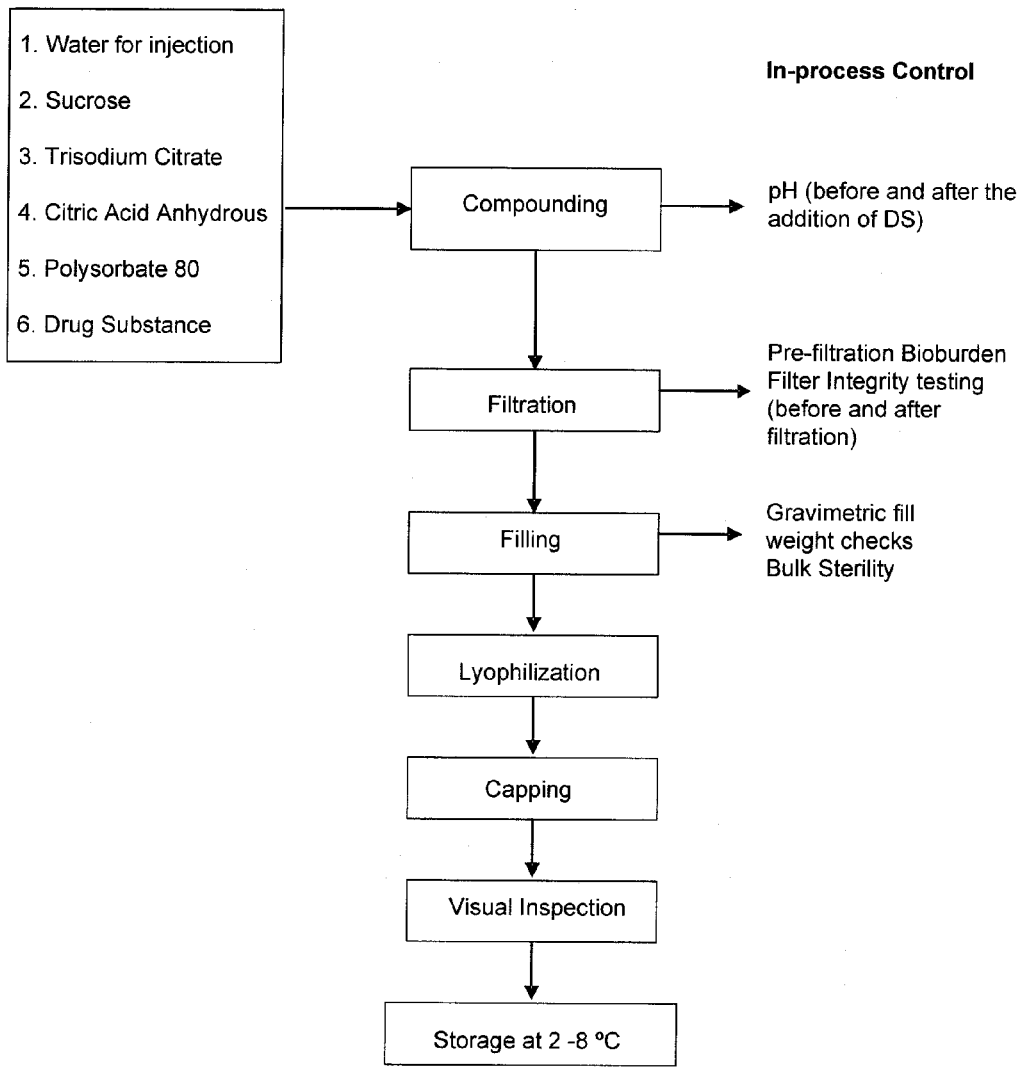
FIG. 1 provides a flow diagram of a manufacturing process for the lyophilized formulation of an anti-IL-23p19 antibody of the present invention. The process is described more fully at Example 1, infra.

As used herein, including the appended claims, the singular forms of words such as "a," "an," and "the," include their corresponding plural references unless the context clearly dictates otherwise. Table 6 below provides a listing of sequence identifiers used in this application. Unless otherwise indicated, the proteins and subjects referred to herein are human proteins and subject, rather than another species.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R.§1.57(b)(1), to relate to each and every individual publication, database entry (e.g. Genbank sequences or GeneID entries), patent application, or patent, each of which is clearly identified in compliance with 37 C.F.R.§1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention provides lyophilized formulations of engineered anti-IL-23 antibodies and uses thereof to treat inflammatory, autoimmune, and proliferative disorders. In some embodiments, the lyophilized formulations of the present invention comprise a humanized anti-IL-23p19 antibody, or binding fragment thereof, as disclosed in co-pending, commonly assigned International Patent Publication No. WO 2008/103432, the disclosure of which is hereby incorporated by reference.

I. Definitions

"Proliferative activity" encompasses an activity that promotes, that is necessary for, or that is specifically associated with, e.g., normal cell division, as well as cancer, tumors, dysplasia, cell transformation, metastasis, and angiogenesis.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "IL-23p19 binding fragment," "antigen binding fragment thereof," "binding fragment thereof" or "fragment thereof" encompass a fragment or a derivative of an antibody that still substantially retains its biological activity of binding to antigen (human IL-23p19) and inhibiting its activity. Therefore, the term "antibody fragment" or IL-23p19 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its IL-23p19 inhibitory activity. Preferably, a binding fragment or derivative retains at least 25%, 50%, 60%, 70%, 80%, 90%, 95%, 99% or 100% (or more) of its IL-23p19 inhibitory activity, although any binding fragment with sufficient affinity to exert the desired biological effect will be useful. It is also intended that a IL-23p19 binding fragment can include variants having conservative amino acid substitutions that do not substantially alter its biologic activity.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific. As used herein, the term "bispecific antibody" refers to an antibody, typically a monoclonal antibody, having binding specificities for at least two different antigenic epitopes, e.g., IL-23p19 and IL-17. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) Science 229:81. Bispecific antibodies include bispecific antibody fragments. See, e.g., Holliger et al. (1993) Proc. Natl. Acad. Sci. U.S.A. 90:6444-48, Gruber et al. (1994) J. Immunol. 152:5368.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies (e.g. hum13B8) from parental rodent antibodies (e.g. mouse 13B8, or m13B8). The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Binding compound," as used herein, refers to a human or humanized antibody that binds to human IL-23p19, or any antigen-binding fragment or derivative of such antibody.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |

TABLE 1-continued

Exemplary Conservative Amino Acid Substitutions

| Original residue | Conservative substitution |
|---|---|
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

A "reconstituted" formulation is one that has been prepared by dissolving a lyophilized protein formulation in a diluent such that the protein is dispersed in the reconstituted formulation. The reconstituted formulation is suitable for administration, e.g. parenteral administration), and may optionally be suitable for subcutaneous administration.

An "isotonic" formulation has essentially the same osmotic pressure as human blood. Isotonic formulations will generally have an osmotic pressure from about 250 to 350 mOsm. Isotonicity can be measured, for example, using a vapor pressure or ice-freezing type osmometer.

II. Human or Humanized Anti-IL-23p19 Antibodies

The lyophilized formulation of the present invention may be used with antibodies generally, including human or humanized anti-human IL-23p19 antibodies, such as those disclosed herein. Humanized forms of anti-human IL-23p19 antibody 13B8 are provided. A hybridoma expressing antibody 13B8 was deposited pursuant to the Budapest Treaty with American Type Culture Collection (ATCC—Manassas, Va., USA) on Aug. 17, 2006 under Accession Number PTA-7803. Humanized forms of other antibodies disclosed herein may be constructed by substituting the human frameworks disclosed for the humanized 13B8 antibody. Substitution with the human frameworks disclosed herein as part of humanized antibody 13B8 is most appropriate for antibodies with CDR sequences similar to 13B8.

Sequences are provided for anti-human IL-23p19 antibodies m1A11, m11C1, m5F5, m21D1, m13B8, h13B8a, h13B8b and h13B8c. CDRs are provided under separate sequence identifiers, as indicated in Table 6. When referring to the antibodies, an "m" prefix connotes a murine antibody and an "h" connotes a humanized antibody. The suffixes "a", "b" and "c" refer to sequence variants of the humanized 13B8 heavy chain variable domain, as discussed in greater detail below.

Ordinarily, amino acid sequence variants of the humanized anti-IL-23 antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95, 98, or 99%. Identity or homology with respect to this sequence is defined herein as the percentage of amino acid residues in the candidate sequence that are identical with the humanized anti-IL-23 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Structure-function data are provided herein for anti-IL-23p19 antibodies of the present invention as follows. One of skill in the art would recognize that alteration of the CDR sequences would be expected to have the most dramatic effects on antigen-binding affinity. Murphy et al., JANEWAY'S IMMUNOBIOLOGY, Seventh Ed., 2008, Chapter 3. The CDR regions for the anti-IL-23p19 antibodies of the present invention are provided in the sequence listing. In addition, comparison of the antibodies disclosed herein to each other can be used to determine which residues are most critical to antigen binding, and thus biological activity. In addition, the invention provides for several sequence variants for the 13B8 antibody, including heavy chain variants 13B8 HC-a, 13B8 HC-b and 13B8 HC-c, providing the original murine CDRH2 sequence (13B8 HC-a) and two variants thereof. See Table 2.

The human or humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

Likewise, either class of light chain can be used in the compositions and methods herein. Specifically, kappa, lambda, or variants thereof are useful in the present compositions and methods.

CDR and FR residues are determined according to the standard sequence definition of Kabat. Kabat et al. (1987) Sequences of Proteins of Immunological Interest, National Institutes of Health, Bethesda Md. SEQ ID NOs: 1-5 show the heavy chain variable domain sequences of various mouse anti-human IL-23p19 antibodies, and SEQ ID NOs: 9-13 depict the light chain variable domain sequences. FIGS. 1 and 2 provide sequence lineups of heavy and light chain variable domains of the various antibodies of the present invention. CDRs are indicated in the figures, and the individual CDR sequences are each presented with unique Sequence Identifiers as indicated in Table 6.

Humanized forms of antibody 13B8 are provided. The humanized light chain 13B8 sequence (with kappa constant region) is provided at SEQ ID NO: 14, and the light chain variable domain comprises residues 1-108 of that sequence. Three versions of the humanized heavy chain 13B8 sequence (with γ1 constant regions) are provided at SEQ ID NOs: 6-8, and the heavy chain variable domain comprises residues 1-116 of those sequences. The 13B8 heavy chains variants are illustrated at Table 2, with differences from the parental sequence noted in bold. The Met (M) was modified to Lys (K) to avoid the potential for oxidation of the residue and inactivation of the antibody. The substitution of AQKLQ for NEMFE is a replacement of the murine CDR sequence with the human germline sequence from the human framework selected to humanize the antibody.

TABLE 2

Antibody 13B8 CDRH2 Variants

| Antibody | CDRH2 Sequence | SEQ ID NO: |
|---|---|---|
| m13B8, h13B8-a | QIFPASGSADYNEMFEG | 24 |
| h13B8-b | QIFPASGSADYNEKFEG | 25 |
| h13B8-c | QIFPASGSADYAQKLQG | 26 |

Humanized forms of the other antibodies disclosed herein may be created by simply substituting the parental rodent antibody CDRs into the light and heavy chain sequences for humanized 13B8 provided at SEQ ID NOs: 14 and 6. This approach is most likely to be successful for antibody chains with CDRs having high homology with the CDRs of antibody 13B8, e.g. clone 11C1 on the heavy chain and clones 11C1 and 21D1 on the light chain. Alternatively, the murine antibodies may be independently humanized using the approaches outlines herein, e.g. at Example 1.

In one embodiment, CDRs include variants of any single sequence CDR disclosed herein (SEQ ID NOs: 15-46), in which the variant comprises 1, 2, 3, 4, 5, 6, 7, 8, 9, 10 or more conservative amino acid substitutions relative to the disclosed sequence, as determined using the data of Table 1.

Heavy and Light chain sequences (SEQ ID NOs: 6-8 and 16) are provided without signal sequences. Exemplary heavy and light chain signal sequences are provided at SEQ ID NOs: 51 and 52, respectively. The signal sequences, or nucleic acid sequences encoding the signal sequences, may be appended to the N-terminus of the respective antibody chains to create a precursor protein for secretion from a host cell. Alternative signal sequences may also be used, and several can be found at "SPdb: a Signal Peptide Database." Choo et al. (2005) *BMC Bioinformatics* 6:249.

III. Biological Activity of Humanized Anti-IL-23

Inflammatory diseases of the skin, joints, CNS, as well as proliferative disorders elicit similar immune responses, thus IL-23 blockade should provide inhibition of these immune mediated inflammatory disorders, without comprising the host ability to fight systemic infections. Antagonizing IL-23 should relieve the inflammation associated with inflammatory bowel disease, Crohn's disease, Ulcerative Colitis, rheumatoid arthritis, psoriatic arthritis, psoriasis, ankylosing spondylitis, and atopic dermatitis. Use of IL-23 inhibitors will also provide inhibition of proliferative disorders, e.g., cancer and autoimmune disorders, e.g., multiple sclerosis, type I diabetes, and SLE. Descriptions of IL-23 in these various disorders can be found in the following published PCT applications: WO 04/081190; WO 04/071517; WO 00/53631; and WO 01/18051. IL-23 inhibitors may also find use in treatment of infections, including chronic infections, such as bacterial, mycobacterial, viral and fungal infections.

The lyophilized formulations of the present invention include antibodies and fragments thereof that are biologically active when reconstituted. As used herein, the term "biologically active" refers to an antibody or antibody fragment that is capable of binding the desired the antigenic epitope and directly or indirectly exerting a biologic effect. Typically, these effects result from the failure of IL-23 to bind its receptor. As used herein, the term "specific" refers to the selective binding of the antibody to the target antigen epitope. Antibodies can be tested for specificity of binding by comparing binding to IL-23 to binding to irrelevant antigen or antigen mixture under a given set of conditions. If the antibody binds to IL-23 at least 10, and preferably 50 times more than to irrelevant antigen or antigen mixture then it is considered to be specific. An antibody that binds to IL-12 is not an IL-23-specific antibody. An antibody that "specifically binds" to IL-23p19 does not bind to proteins that do not comprise the IL-23p19-derived sequences, i.e. "specificity" as used herein relates to IL-23p19 specificity, and not any other sequences that may be present in the protein in question. For example, as used herein, an antibody that "specifically binds" to IL-23p19 will typically bind to FLAG®-hIL-23p19, which is a fusion protein comprising IL-23p19 and a FLAG® peptide tag, but it does not bind to the FLAG® peptide tag alone or when it is fused to a protein other than IL-23p19.

IL-23-specific binding compounds of the present invention, such as inhibitory IL-23p19 specific antibodies, can inhibit its biological activity in any manner, including but not limited to production of IL-1β and TNF by peritoneal macrophages and IL-17 by $T_H17$ T cells. See Langrish et al. (2004) *Immunol. Rev.* 202:96-105. Anti-IL-23p19 antibodies will also be able to inhibit the gene expression of IL-17A, IL-17F, CCL7, CCL17, CCL20, CCL22, CCR1, and GM-CSF. See Langrish et al. (2005) *J. Exp. Med.* 201:233-240. IL-23-specific binding compounds of the present invention, such as anti IL-23p19 antibodies, will also block the ability of IL-23 to enhance proliferation or survival of $T_H17$ cells. Cua and Kastelein (2006) *Nat. Immunol.* 7:557-559. The inhibitory activity of engineered anti-IL-23p19 will be useful in the treatment of inflammatory, autoimmune, and proliferative disorders. Examples of such disorders are described in PCT patent application publications WO 04/081190; WO 04/071517; WO 00/53631; and WO 01/18051.

The formulation of the present invention is useful, for example, for storage and transport of human or humanized anti-IL-23p19 antibodies (or antigen binding fragments thereof) for use in treatment or prevention of a disorder associated with elevated activity of IL-23 or IL-23p19, such as Th17-mediated diseases, autoimmune or chronic inflammatory disorders, or cancers.

IV. Lyophilized Pharmaceutical Compositions

Lyophilized formulations of therapeutic proteins provide several advantages. Lyophilized formulations in general offer better chemical stability than solution formulations, and thus increased half-life. A lyophilized formulation may also be reconstituted at different concentrations depending on clinical factors, such as route of administration or dosing. For example, a lyophilized formulation may be reconstituted at a high concentration (i.e. in a small volume) if necessary for subcutaneous administration, or at a lower concentration if administered intravenously. High concentrations may also be necessary if high dosing is required for a particular subject, particularly if administered subcutaneously where injection volume must be minimized. One such lyophilized antibody formulation is disclosed at U.S. Pat. No. 6,267,958, which is hereby incorporated by reference in its entirety. Lyophilized formulations of another therapeutic protein are disclosed at U.S. Pat. No. 7,247,707, which is hereby incorporated by reference in its entirety.

Typically the lyophilized formulation is prepared in anticipation of reconstitution at high concentration of drug product (DP, in this case human or humanized anti-IL-23p19 antibody, or antigen binding fragment thereof), i.e. in anticipation of reconstitution in a low volume of water. Subsequent dilution with water or isotonic buffer can then readily be used to dilute the DP to a lower concentration. Typically, excipients are included in a lyophilized formulation of the present invention at levels that will result in a roughly isotonic formulation when reconstituted at high DP concentration, e.g. for subcutaneous administration. Reconstitution in a larger volume of water to give a lower DP concentration will necessarily reduce the tonicity of the reconstituted solution, but such reduction may be of little significance in non-subcutaneous, e.g. intravenous, administration. If isotonicity is desired at lower DP concentration, the lyophilized powder may be reconstituted in the standard low volume of water and then further diluted with isotonic diluent, such as 0.9% sodium chloride.

In one embodiment of the present invention, human or humanized anti-IL-23p19 antibody (or antigen binding fragment thereof) is formulated as a lyophilized powder for subcutaneous or intravenous administration. One such formulation is provided at Table 3 and described at Example 1. In one embodiment, the antibody (or antigen binding fragment thereof) is provided at about 50 mg/vial, and is reconstituted with sterile water for injection prior to use. If desired, the reconstituted antibody may be aseptically diluted with water or 0.9% Sodium Chloride Injection USP in a sterile IV container. The target pH of the reconstituted formulation is 4.8±0.4, or optionally 4.8±0.2. In various embodiments, the lyophilized formulation of the present invention enables reconstitution of the human or humanized anti-IL-23p19 antibody to high concentrations, such as about 20, 25, 30, 40, 50, 60, 75, 100 or more mg/mL.

The present invention provides, inter alia, a lyophilized formulation comprising a human or humanized anti-IL-23p19 antibody, a citrate buffer at about pH 4.8, or at about pH 5.5, for example about 3.5, 3.8, 4.2, 4.6, 4.7, 4.8, 4.9, 5.0, 5.2, 5.5 or 5.8, more preferably about 4.6, 4.7, 4.8, 4.9 or 5.0. When a range of pH values is recited, such as "a pH between pH 4.4 and 5.2," the range is intended to be inclusive of the recited values. Unless otherwise indicated, the pH refers to the pH after reconstitution of the lyophilized formulations of the present invention. The pH is measured at 25° C. using standard glass bulb pH meter. As used herein, a solution comprising "citrate buffer at pH X" refers to a solution at pH X and comprising the citrate buffer, i.e. the pH is intended to refer to the pH of the solution.

The formulations in Tables 3 and 4 (Example 1) reflect the weight of the components in a batch formulation, as lyophilized in vials, and as reconstituted. Lyophilized formulations are by definition essentially dry, and thus the concept of concentration is not useful in describing them. Describing a lyophilized formulation in the terms of the weight of the components in a unit dose vial is more useful, but is problematic because it varies for different doses or vial sizes. In describing the lyophilized formulations of the present invention, it is useful to express the amount of a component as the ratio of the weight of the component compared to the weight of the drug substance (DS) in the same sample (e.g. a vial). This ratio may be expressed as a percentage. Such ratios reflect an intrinsic property of the lyophilized formulations of the present invention, independent of vial size, dosing, and reconstitution protocol.

In other embodiments, the lyophilized formulation of anti-human IL-23p19 antibody, or antigen binding fragment, is defined in terms of the pre-lyophilization solution used to make the lyophilized formulation, such as the pre-lyophilization solution disclosed at Table 3. Pre-lyophilization solutions may comprise antibody, or antigen-binding fragment thereof, at concentrations of about 1, 3, 5, 10, 15, 20, 25, 30, 40, 50 mg/mL or higher. Such pre-lyophilization solutions may be at pH 4.4-5.2, e.g. about pH 4.8, or may be at about pH 5.5.

In yet other embodiments, the lyophilized formulation of anti-human IL-23p19 antibody, or antigen binding fragment, is defined in terms of the reconstituted solution generated from the lyophilized formulation, such as the reconstituted solution disclosed at Table 4. Reconstituted solutions may comprise antibody, or antigen-binding fragment thereof, at concentrations of about 10, 15, 20, 25, 30, 40, 50, 60, 75, 80, 90 or 100 mg/mL or higher. Such reconstituted solutions may be at pH 4.4-5.2, e.g. about pH 4.8, or may be at about pH 5.5.

The lyophilized formulations of the present invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will dictate the time required for drying, which can range from a few hours to several days (e.g. 40-60 hrs). A secondary drying stage may be carried out at about 0-40° C., depending primarily on the type and size of container and the type of protein employed. The secondary drying time is dictated by the desired residual moisture level in the product and typically takes at least about 5 hours (e.g. 10-15 hours). Typically, the moisture content of a lyophilized formulation is less than about 5%, and preferably less than about 3%. The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

The lyophilized formulations of the present invention are reconstituted prior to administration. The protein may be reconstituted at a concentration of about 10, 15, 20, 25, 30, 40, 50, 60, 75, 80, 90 or 100 mg/mL or higher. High protein concentrations are particularly useful where subcutaneous delivery of the reconstituted formulation is intended. However, for other routes of administration, such as intravenous administration, lower concentrations of the protein may be desired (e.g. from about 5-50 mg/mL).

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Various literature references are available to facilitate selection of pharmaceutically acceptable carriers or excipients. See, e.g., *Remington's Pharmaceutical Sciences and U.S. Pharmacopeia: National Formulary*, Mack Publishing Company, Easton, Pa. (1984); Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity is a primary consideration is selecting the proper dosing of a therapeutic agent, such as a human or humanized anti-IL-23p19 antibody (or antigen binding fragment thereof). Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

Suitable routes of administration may, for example, include oral, rectal, transmucosal, or intestinal administration; parenteral delivery, including intramuscular, intradermal, subcutaneous, intramedullary injections, as well as intrathecal, direct intraventricular, intravenous, intraperitoneal, intranasal, or intraocular injections. Drugs can be administered in a variety of conventional ways, such as oral ingestion, pulmonarily by inhalation, topical application or cutaneous, subcutaneous, intraperitoneal, parenteral, intraarterial or intravenous injection. Modes of administration in which the volume of solution must be limited (e.g. subcutaneous administration) require that a lyophilized formulation enable reconstitution at high concentration.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002).

Determination of the appropriate dose is made by the clinician, e.g., using parameters or factors known or suspected in the art to affect treatment or predicted to affect treatment. The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. The protein is suitably administered to the patient at one time or repeatedly. The protein may be administered alone or in conjunction with other drugs or therapies.

Antibodies, antibody fragments, and cytokines can be provided by continuous infusion, or by doses at intervals of, e.g., one day, 1-7 times per week, one week, two weeks, monthly, bimonthly, etc. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

Subcutaneous administration may performed by injected using a syringe, or using other injection devices (e.g. the Inject-ease® device); injector pens; or needleless devices (e.g. MediJector and BioJector®).

VII. Uses

The present invention provides lyophilized formulations of anti-IL-23 antibodies (and fragments thereof) for use in the treatment of inflammatory disorders and conditions, e.g., of the central nervous system, peripheral nervous system, and gastrointestinal tract, as well as autoimmune and proliferative disorders.

The lyophilized formulations of the present invention can be used in the treatment of, e.g., multiple sclerosis (MS), including relapsing-remitting MS and primary progressive MS, Alzheimer's disease, amyotrophic lateral sclerosis (a.k.a. ALS; Lou Gehrig's disease), ischemic brain injury, prion diseases, and HIV-associated dementia, as well as neuropathic pain, posttraumatic neuropathies, Guillain-Barre syndrome (GBS), peripheral polyneuropathy, and nerve regeneration.

The lyophilized formulations of the present invention can also be used in the treatment of inflammatory bowel disorders, e.g., Crohn's disease, ulcerative colitis, celiac disease, and irritable bowel syndrome. They can also be used in the treatment of inflammatory disorders such as psoriasis, atopic dermatitis, arthritis, including rheumatoid arthritis, osteoarthritis, and psoriatic arthritis, autoimmune disorders, such as systemic lupus erythematosus and type I diabetes, and proliferative disorders such as cancer. See, e.g., PCT patent application publications WO 04/081190; WO 04/071517; WO 00/53631; and WO 01/18051.

The broad scope of this invention is best understood with reference to the following examples, which are not intended to limit the inventions to the specific embodiments. The specific embodiments described herein are offered by way of example only, and the invention is to be defined by the terms of the accompanying claims, along with the full scope of equivalents to which such claims are entitled.

EXAMPLES

Example 1

Lyophilized Formulations of Humanized Anti-IL-23p19 Antibodies

Lyophilized formulations of a humanized anti-human IL-23p19 antibody are prepared as follows. A batch formula for humanized anti-IL-23p19 antibody is provided in Table 3. The final concentration of humanized anti-IL-23p19 antibody is 25 mg/mL. This batch formulation may used to prepare the lyophilized 50 mg/vial units, as discussed with reference to Table 4, infra. Polysorbate 80 from a vegetable source is used. Additional citric acid or sodium hydroxide may be added to adjust the pH to the desired value of approximately 4.8 (±0.2). A pH of 4.8 is used to reduce opalescence when the antibody is reconstituted from citrate buffer at pH 5.5-5.6. The components are brought to a final volume of 40 L with sterile water for injection (WFI). Correspondingly smaller lots may, of course, be prepared by proportional reduction of the amounts listed in Table 3.

TABLE 3

Batch Formula for Anti-IL-23p19 Antibody

| Component | Grade | Amount per Batch (g) |
|---|---|---|
| Humanized Anti-IL-23p19 antibody | — | 1000 |
| Trisodium Citrate Dihydrate | USP | 14.83 |
| Citric Acid (anhydrous) | USP | 9.512 |
| Polysorbate 80 | NF | 2.0 |
| Sucrose | NF | 700 |
| Sodium Hydroxide | NF | pH adjustment |
| Water for injection | USP | q.s. to 40.00 L |

The unit composition of the final lyophilized formulation of humanized anti-IL-23p19 is provided at Table 4.

TABLE 4

Unit Composition of Lyophilized Powder Formulation for Solution for Injection

| Component | Grade | Amount (mg/vial) | Concentration after Reconstitution (mg/mL) | Function |
|---|---|---|---|---|
| Humanized anti-IL-23p19 antibody | — | 50 | 100 | Drug Substance |
| Trisodium Citrate Dihydrate | USP | 0.7414 | 1.483 | Buffer salt |
| Citric Acid (anhydrous) | USP | 0.476 | 0.951 | Buffer acid |
| Polysorbate 80 | NF | 0.10 | 0.20 | Surfactant |
| Sucrose | NF | 35 | 70 | Stabilizer/ Tonicity Modifier |
| Sodium Hydroxide | NF | — | — | pH adjustment |
| Sterile Water for Injection | USP | — | q.s. to 0.5 mL | Solvent |

The unit formulation of Table 4 comprises $1/20,000^{th}$ of the batch formulation of Table 3 after lyophilization to remove the water. The 50 mg of DS is added as 2.0 mL of the 25 mg/mL batch formulation of Table 3, and concentrated four-fold by reconstitution with sterile WFI to a final volume of 0.5 mL. Accordingly, the initial 2.5 mM citrate buffer is concentrated to about 10 mM citrate buffer in the reconstituted solution, and the sucrose is concentrated from about 50 mM to about 200 mM. Lower final concentrations may be obtained by reconstituting in a larger volume of liquid, such as 0.5 mL of WFI and additional amounts of 0.9% sodium chloride or WFI.

In order to ensure consistent delivery of the label fill, product vials may contain an appropriate volume of overfill to compensate for residual product solution that might remain in the vial and the syringe during withdrawal of the reconstituted solution. For example, a nominal fill of 2.0 mL (50 mg) may be increased to an overfill of 2.7 mL (67.5 mg). In the event of such overfill, the final unit composition will, of course, comprise proportionally greater amounts of each component listed in Table 4. In the case of a 2.7 mL fill for a nominal 2.0 mL vial, the amount of each component would be 35% higher than listed in Table 4, as illustrated in Table 5. For a 2.7 mL overfill, 0.56 mL of water is used for reconstitution to a final volume of 0.675 mL, for a final concentration of 100 mg/mL. The final concentrations after reconstitution are, of course, the same as in Table 4.

TABLE 5

2.7 mL Overfill Unit Composition

| Component | Grade | Amount (mg/vial) | Concentration after Reconstitution (mg/mL) | Function |
|---|---|---|---|---|
| Humanized anti-IL-23p19 antibody | — | 67.5 | 100.0 | Active Pharmaceutical Ingredient (API) |
| Trisodium Citrate Dihydrate | USP | 1.001 | 1.483 | Buffer salt |
| Citric Acid (anhydrous) | USP | 0.643 | 0.951 | Buffer acid |
| Polysorbate 80 | NF | 0.135 | 0.200 | Surfactant |
| Sucrose | NF | 47.25 | 70.00 | Stabilizer/ Tonicity Modifier |
| Sodium Hydroxide | NF | — | — | pH adjustment |
| Sterile Water for Injection | USP | — | 0.56 mL. | Solvent |

The drug is packaged in sterile 13 mm neck, 5 mL, Type 1 glass tubing vials, closed with 13-mm gray butyl rubber stoppers and sealed with aluminum crimp seals with polypropylene bonnet. Vials are stored at 2-8° C., and refrigerated when shipped.

FIG. 1 is a flow diagram for a manufacturing process for the lyophilized formulation of humanized anti-IL-23p19 antibody of the present invention, e.g. into a 50 mg unit dose vial.

Compounding involves the following steps. Charge the required amount of water for injection (WFI) into a tared compounding vessel. Charge and dissolve with mixing, sucrose, trisodium citrate dihydrate, citric acid, and polysorbate 80 from a vegetable source. Measure the pH. Equilibrate the drug substance to ambient temperature and charge the drug substance slowly into the compounding vessel. Continue to mix gently to avoid foaming. Measure the pH again and adjust if needed to bring the pH to approximately 4.8. Charge WFI to the final weight of the bulk solution with continued gentle mixing.

Filtration involves the following steps. Connect sterilizing filter (0.22 μm) to the sterile receiving vessel. Collect an aliquot of the bulk solution for bioburden testing prior to sterile filtration. Perform aseptic filtration using a 0.22 μm filter into a sterile container. Perform filter integrity testing before and after product filtration.

Filling involves the following steps. Using suitable filling equipment, aseptically fill the product solution into sterilized Type I tubing glass vials to achieve a target fill volume of 2.7 ml. Perform fill weight checks during filling. Remove appropriate number of vials at beginning of filling and pool the solution for bulk sterility and endotoxin testing. Partially seat sterilized lyo-shape stoppers into filled vials. Load the filled vials into a suitable freeze-dryer.

Lyophilization, stoppering and capping involve the following steps. Lyophilize the filled vials using an appropriate lyophilization cycle. After lyophilization is complete, backfill the vials with 0.22 µm filtered nitrogen and fully stopper. Unload the stoppered vials from the lyophilizer and seal them.

The resulting vials are inspected for visual defects and stored at 2-8° C. Finished unit dosage vials are shipped under refrigerated conditions.

Example 2

Stability Testing of Lyophilized Formulations of Humanized Anti-IL-23p19 Antibodies FIGS. 2-7 provide the results of stability testing of lyophilized formulations of a humanized anti-human IL-23p19 antibody under various storage conditions. Some vials were stored in both upright and inverted configurations, as indicated in the figures. As discussed in more detail below, FIGS. 2-4 show stability of at least 18 months for antibodies lyophilized at pH 5.5 (citrate buffer), and FIGS. 5-7 show stability of at least 12 months for antibodies lyophilized at pH 4.8 (citrate buffer), wherein 18- and 12-months are the longest time points presented rather than an experimentally determined stability endpoint.

Stability was assessed as follows. Samples were lyophilized in 5 mL Type I glass vials, and sealed with 13 mm bromobutyl lyo stoppers (Helvoet Rubber & Plastic Technologies BV, Hellevoetsluis, The Netherlands) and flip-off aluminum seals. B2-Coated 13 mm gray butyl lyo-stoppers (West Pharmaceutical Services Inc., Lionville, Pa., USA) may also be used. Vials were placed on stability stations under the following storage conditions: 5C (5±3° C.), 25H (25, 60% relative humidity), or RH4 (40° C., 70% relative humidity). Samples were obtained at an initial time point, and at 0.5, 1, 2, 3, 6, 9, 12 or 18 months, as indicated in the figures.

The stability of the samples is illustrated by the various characteristics presented at FIGS. 2-7. The lyophilized samples were visually inspected, reconstituted, and the reconstituted formulation was visually inspected. The pH of the samples after reconstitution was measured, and the protein concentration determined by U.V. absorbance. The samples were then analyzed by denaturing sodium dodecyl sulfate (SDS) polyacrylamide gel electrophoresis (PAGE), with the level of impurities (i.e. material other than the main product band) expressed as the percentage of the total intensity in each lane. Purity of the sample was further assessed by high performance size exclusion chromatography (HPSEC) in which the percentage of monomer was determined, as well as the percentages of high molecular weight species (possibly aggregates) and late eluting peaks (possibly degradation products).

Additional sample characterization data include high performance ion-exchange chromatography (HP-IEX), which is used to assess purity by revealing the presence of acidic or basic variants. Results are presented as a percentage of total observed material. The samples were further characterized for biological function using an enzyme-linked immunosorbent assay (ELISA) for binding to human IL-23p19. Results are expressed as the $EC_{50}$ for the sample, i.e. the concentration necessary to achieve half-maximal binding. Results are also provided as a percentage potency relative to control, calculated as the 100 times the ratio of $EC_{50}$ for the samples to the $EC_{50}$ for a control preparation of the same antibody. Moisture content of the lyophilized powder was also determined.

Data in FIGS. 2, 3 and 4 were obtained for samples at pH 5.5 when stored at 5C, 25H, and RH4, respectively. Data in FIGS. 5, 6 and 7 were obtained for samples at pH 4.8 when stored at 5C, 25H, and RH4, respectively.

The results generally demonstrate high stability of lyophilized formulations of the present invention over 1, 3, 6, 9, 12 and 18 month time periods, at both pH 5.5 and 4.8. The data reveal no trending over time that would reflect instability for samples at refrigerated storage conditions. Based on these results, samples are projected to have a shelf-life of at least 24 months.

Table 6 provides a brief description of the sequences in the sequence listing.

TABLE 6

| Sequence Identifiers | |
|---|---|
| SEQ ID NO: | Description |
| 1 | m1A11 $V_H$ |
| 2 | m11C1 $V_H$ |
| 3 | m5F5 $V_H$ |
| 4 | m21D1 $V_H$ |
| 5 | m13B8 $V_H$ |
| 6 | hum13B8 HC-a |
| 7 | hum13B8 HC-b |
| 8 | hum13B8 HC-c |
| 9 | m1A11 $V_L$ |
| 10 | m11C1 $V_L$ |
| 11 | m5F5 $V_L$ |
| 12 | m21D1 $V_L$ |
| 13 | m13B8 $V_L$ |
| 14 | hum13B8 LC |
| 15 | m1A11 CDRH1 |
| 16 | m11C1 CDRH1 |
| 17 | m5F5 CDRH1 |
| 18 | m21D1 CDRH1 |
| 19 | m13B8 CDRH1 |
| 20 | m1A1 CDRH2 |
| 21 | m11C1 CDRH2 |
| 22 | m5F5 CDRH2 |
| 23 | m21D1 CDRH2 |
| 24 | m13B8 CDRH2-a |
| 25 | h13B8 CDRH2-b |
| 26 | h13B8 CDRH2-c |
| 27 | m1A1 CDRH3 |
| 28 | m11C1 CDRH3 |
| 29 | m5F5 CDRH3 |
| 30 | m21D1 CDRH3 |
| 31 | m13B8 CDRH3 |
| 32 | m1A11 CDRL1 |
| 33 | m11C1 CDRL1 |
| 34 | m5F5 CDRL1 |
| 35 | m21D1 CDRL1 |
| 36 | m13B8 CDRL1 |
| 37 | m1A11 CDRL2 |
| 38 | m11C1 CDRL2 |
| 39 | m5F5 CDRL2 |
| 40 | m21D1 CDRL2 |
| 41 | m13B8 CDRL2 |
| 42 | m1A11 CDRL3 |
| 43 | m11C1 CDRL3 |
| 44 | m5F5 CDRL3 |
| 45 | m21D1 CDRL3 |
| 46 | m13B8 CDRL3 |

TABLE 6-continued

Sequence Identifiers

| SEQ ID NO: | Description |
|---|---|
| 47 | human IL-23p19 |
| 48 | mouse IL-23p19 |
| 49 | hum13B8-b HC DNA |
| 50 | hum13B8 LC DNA |

TABLE 6-continued

Sequence Identifiers

| SEQ ID NO: | Description |
|---|---|
| 51 | Heavy Chain Signal Sequence |
| 52 | Light Chain Signal Sequence |

What is claimed is:

1. A lyophilized formulation of an anti-human IL-23p19 antibody, or antigen binding fragment thereof, comprising:
   a) said anti-human IL-23p19 antibody, or antigen binding fragment thereof;
   b) sodium citrate;
   c) polysorbate 80; and
   d) sucrose
   wherein the antibody, or antigen binding fragment thereof, comprises:
   i) a light chain comprising CDRL1, CDRL2 and CDRL3, wherein:
      CDRL1 comprises the sequence of SEQ ID NO:36;
      CDRL2 comprises the sequence of SEQ ID NO:41; and
      CDRL3 comprises the sequence of SEQ ID NO:46; and
   ii) a heavy chain comprising CDRH1, CDRH2 and CDRH3, wherein:
      CDRH1 comprises the sequence of SEQ ID NO:19;
      CDRH2 comprises a sequence selected from the group consisting of SEQ ID NOs:24-26; and
      CDRH3 comprises the sequence of SEQ ID NO:31.

2. The lyophilized formulation of claim 1, wherein the formulation has a pH between 4.4 and 5.2 when reconstituted.

3. The lyophilized formulation of claim 1 that enables reconstitution of the antibody, or antigen binding fragment thereof, at a concentration of 100 mg/mL.

4. The lyophilized formulation of claim 1, wherein polysorbate 80 is present at a weight ratio of approximately 0.2% compared to the antibody or antigen binding fragment thereof.

5. The lyophilized formulation of claim 1, wherein sucrose is present at a weight ratio of approximately 70% compared to the antibody, or antigen binding fragment thereof.

6. A lyophilized pharmaceutical formulation of an anti-human IL-23p19 antibody, or antigen binding fragment thereof, made by lyophilizing an aqueous solution comprising:
   a) 5-25 mg/mL anti-human IL-23p19 antibody, or antigen binding fragment thereof;
   b) about 50 mM sucrose;
   c) about 0.05 mg/mL polysorbate 80; and
   d) about 2.5 mM citrate buffer at pH 4.4-5.2,
   wherein the antibody, or antigen binding fragment thereof, comprises:
   i) a light chain comprising CDRL1, CDRL2 and CDRL3, wherein:
      CDRL1 comprises the sequence of SEQ ID NO:36;
      CDRL2 comprises the sequence of SEQ ID NO:41; and
      CDRL3 comprises the sequence of SEQ ID NO:46;
      and
   ii) a heavy chain comprising CDRH1, CDRH2 and CDRH3, wherein:

CDRH1 comprises the sequence of SEQ ID NO:19;

CDRH2 comprises a sequence selected from the group consisting of SEQ ID NOs:24-26; and CDRH3 comprises the sequence of SEQ ID NO:31.

7. The lyophilized pharmaceutical formulation of claim 6, wherein the anti-human IL-23p19 antibody, or antigen binding fragment thereof, is present at about 25 mg/mL in the aqueous solution.

8. The lyophilized pharmaceutical formulation of claim 6, wherein the aqueous solution has a pH of about 4.8.

9. A lyophilized pharmaceutical formulation of an anti-human IL-23p19 antibody, or antigen binding fragment thereof, that when reconstituted comprises:
   a) 25-100 mg/mL anti-human IL-23p19 antibody, or antigen binding fragment thereof;
   b) about 200 mM sucrose;
   c) about 0.2 mg/mL polysorbate 80; and
   d) about 10 mM citrate buffer at pH 4.4 to 5.2,
   wherein the antibody, or antigen binding fragment thereof, comprises:
   i) a light chain comprising comprising CDRL1, CDRL2 and CDRL3, wherein:
   CDRL1 comprises the sequence of SEQ ID NO:36;
   CDRL2 comprises the sequence of SEQ ID NO:41; and
   CDRL3 comprises the sequence of SEQ ID NO:46; and
   ii) a heavy chain comprising CDRH1, CDRH2 and CDRH3, wherein:
   CDRH1 comprises the sequence of SEQ ID NO:19;
   CDRH2 comprises a sequence selected from the group consisting of SEQ ID NOs:24-26; and
   CDRH3 comprises the sequence of SEQ ID NO:31.

10. The lyophilized pharmaceutical formulation of claim 9, wherein the anti-human IL-23p19 antibody, or antigen binding fragment thereof, is present at about 100 mg/mL in the reconstituted solution.

11. The lyophilized pharmaceutical formulation of claim 9, wherein the reconstituted solution has a pH of about 4.8.

12. The lyophilized formulation of any one of claim 1, 6 or 9, wherein the antibody, or antigen binding fragment thereof, comprises a light chain variable domain comprising residues 1-108 of SEQ ID NO: 14.

13. The lyophilized formulation of any one of claim 1, 6 or 9, wherein the antibody, or antigen binding fragment thereof, comprises a heavy chain variable domain comprising a sequence selected from the group consisting of residues 1-116 of SEQ ID NOs: 6-8.

14. The lyophilized formulation of any one of claim 1, 6 or 9, wherein the antibody, or antigen binding fragment thereof, comprises:
   i) a light chain comprising SEQ ID NO: 14; and
   ii) a heavy chain comprising a sequence selected from the group consisting of SEQ ID NOs: 6-8.

* * * * *